United States Patent [19]
Deleeuw et al.

[11] Patent Number: 5,652,376
[45] Date of Patent: Jul. 29, 1997

[54] METHOD OF MEASURING YIELD STRESS

[75] Inventors: David Charles Deleeuw; Neal Roger Langley, both of Midland, Mich.

[73] Assignee: Dow Corning Corporation, Midland, Mich.

[21] Appl. No.: 676,018

[22] Filed: Jul. 5, 1996

[51] Int. Cl.$^6$ .................................................. G01N 11/14
[52] U.S. Cl. ............................................. 73/54.35; 73/843
[58] Field of Search ................................. 73/807, 54.28, 73/54.34, 54.35, 54.01, 843

[56] References Cited

U.S. PATENT DOCUMENTS

| | | | |
|---|---|---|---|
| 3,035,016 | 5/1962 | Bruner | 260/46 |
| 3,077,465 | 2/1963 | Bruner | 260/46 |
| 3,274,145 | 9/1966 | Dupree | 260/37 |
| 3,473,367 | 10/1969 | Troland et al. | 73/54.01 |
| 3,569,722 | 3/1971 | Denson | 73/54.01 X |
| 3,800,597 | 4/1974 | Paul et al. | 73/54.35 X |
| 4,115,356 | 9/1978 | Hilliard | 528/18 |
| 4,466,274 | 8/1984 | Starr, Jr. | 73/54.01 |
| 4,559,812 | 12/1985 | Kitchen | 73/843 X |
| 4,633,708 | 1/1987 | Blommaert | 73/54.35 |
| 4,736,624 | 4/1988 | Arnstein et al. | 73/54.35 |
| 4,760,734 | 8/1988 | Maxwell | 73/54.34 |
| 5,520,042 | 5/1996 | Garritano et al. | 73/843 X |

OTHER PUBLICATIONS

Rheol, Acta 21, 325–332 (1982).
Journal of Rheology, 29 (3), 335–347, (1985).
Journal of Rheology, 31 (8), 699–710, (1987).
Biotechnology & Bioengineering, vol. 40, pp. 403–412 (1992).
Surface Coatings International, vol. 77, No. 8, 347–351 (1994).
Journal of Colloid Science, vol. 6, 171, (1951).
Journal of Rheology, 27 (4), 321, (1983).
ASTM Standard Test Method for Slump of Sealants D2202.

*Primary Examiner*—Elizabeth L. Dougherty
*Attorney, Agent, or Firm*—James L. DeCesare

[57] ABSTRACT

The yield stress of rheologically plastic fluids such as coatings, sealants, and personal care lotions, determines their tendency to flow at low gravitational stress. Yield Stress is the apparent threshold stress above which flow is observed on an arbitrary time scale. An on-line technique to monitor yield stress during processing was developed, and can be used in controlling the slump or non-slump behavior of such products. A residual stress, after a flow excursion returns to zero shear rate, is related to yield stress. This residual stress can be used for process monitoring. It is measured from the residual pressure or torque after a controlled strain rheometer reaches zero strain rate.

10 Claims, 2 Drawing Sheets

METHOD OF MEASURING YIELD STRESS

BACKGROUND OF THE INVENTION

This invention relates to a method of measuring yield stress in polymer systems. The method was developed and demonstrated using an on-line capillary rheometer. Such a method of measurement has utility in on-line assurance testing of production processes, and could be a suitable replacement for currently used test methods performed off-line.

Rheology is the science of flow and possible elastic deformation of matter. It is concerned with the response of materials to a mechanical force. The flow properties of a simple viscous liquid are defined by its resistance to flow, i.e., viscosity, and may be measured by determining the rate of flow through a capillary.

Such a simple viscous liquid continues to deform as long as it is subjected to a tensile stress or a shear stress. Shear stress is a force applied tangentially to the material. In a liquid, shear stress produces a sliding of one infinitesimal layer over another.

For a liquid under shear, the rate of deformation or shear rate is proportional to the shearing stress. This is true for ideal or Newtonian liquids, i.e. water, but the viscosity of many liquids is not independent of shear rate. Non-Newtonian liquids may be classified according to their viscosity behavior as a function of shear rate. Some liquids exhibit shear thinning, whereas other liquids exhibit shear thickening. Some liquids at rest appear to behave like elastic solids until the shear stress exceeds a certain value called the yield stress ($tau_0$), after which they flow readily.

Elastic as well as viscous behavior can be observed at the onset or cessation of flow when the applied stress is insufficient to initiate or sustain flow, respectively. The minimum stress required to initiate flow is referred to as yield stress, while the maximum stress observed at the cessation of flow can be referred to as residual stress. Yield stress and residual stress are not necessarily equal. Their values are subject to flow rate and flow history considerations. However, on a reasonable time scale, their values can be considered to be proportional and approximately equal for most materials. For purposes of this invention, specific measurements of residual stress were made, but the results have been reported generically in terms of yield stress.

Shear stress is often plotted against shear rate on plots called flow curves which are used to express the rheological behavior of liquids. Newtonian flow is shown by a straight line, and shear thinning and shear thickening are shown by curves. Yield stress is an intercept or point on the stress (tau) axis of such plots (see FIG. 2 in the drawing, for example). Yield stress, therefore, is a parameter which can be quite useful in characterizing materials. For example, water has a yield stress of zero.

A method for measuring yield stress was discovered while attempting to repeatably calibrate a capillary rheometer. It was discovered that when flow through the capillary was stopped for zero calibration, a residual positive (forward) backpressure proportional to yield stress, remained within the capillary rheometer. By manually reversing the metering pump of the rheometer, a negative (reverse) backpressure was noted. The difference between the positive and negative (forward and reverse) residual pressures is proportional to twice the yield stress, and is independent of the zero calibration value. This discovery was made while using an on-line capillary rheometer for monitoring a silicone sealant mixture.

The mathematical relationship used to make the measurement is defined by the equation:

Shear Stress$_{(Flow)}$ at Capillary Wall=$RP/2L$ where R is the radius of the capillary, L is the length of the capillary, and P is the pressure drop through the capillary.

Thus, for a given system, the pressure P is a proportional measure of the residual stress$_{(No\ Flow)}$ below which flow through the capillary will stop. The most common units for shear stress$_{(Flow)}$, residual stress, and yield stress$_{(No\ Flow)}$, are dynes per square centimeter ($dyn/cm^2$), Pascals (10 $dyn/cm^2$=1 Pa), newtons per square meter ($1N/m^2$=1 Pa), and bar (1 bar=$1\times10^5$ Pa=14.5 psi).

BRIEF SUMMARY OF THE INVENTION

This invention is directed to a method of measuring the residual stress of a polymeric material. The method is carried out by practicing the following steps:

(a) flowing a polymeric material in a forward direction through a capillary passageway so as to produce a positive backpressure (i.e., 17.2 bar in Table I), (b) stopping the flow of polymeric material in the forward direction and allowing the positive backpressure to stabilize and reach a constant value (i.e., +0.20 bar in Table I), (c) recording the positive backpressure under no flow conditions at the constant value reached in step (b), (d) flowing the polymeric material in a reverse direction through the capillary passageway so as to produce a negative backpressure, (e) stopping the flow of polymeric material in the reverse direction and allowing the negative backpressure to stabilize and reach a constant value (i.e., −1.07 bar in Table I), (f) recording the negative backpressure under no flow conditions at the constant value reached in step (e), (h) determining half the difference between the positive backpressure (+0.20 bar) and the negative backpressure (−1.07 bar) as the pressure drop (0.635 bar) through the capillary passageway, and (i) calculating a residual stress for the polymeric material according to the relationship Residual Stress$_{(No\ Flow)}$= $RP/2L$ where R is the radius of the capillary passageway, L is the length of the capillary passageway, and P is the pressure drop through the capillary passageway determined in step (h).

In other words, the invention can be described as a method of measuring a residual pressure drop and stress which is considered to be proportionate to the yield stress of a material. The method comprises:

(a) flowing the material in a forward direction through a chamber having an exit through a restricted passageway so as to produce a positive pressure in the chamber, (b) stopping the forward flow of material into the chamber and allowing the residual positive pressure in the chamber to stabilize and reach a constant value, (c) recording the residual positive pressure in the chamber under no flow conditions at the constant value reached in step (b), (d) withdrawing material from the chamber so as to produce a negative pressure and initiate a reverse flow of material into the chamber through the restricted passageway, (e) stopping the withdrawal of material from the chamber and allowing the negative pressure to stabilize and reach a constant value, (f) recording the residual negative pressure in the chamber under no flow conditions at the constant value reached in step (e), (h) determining half the difference between the residual positive pressure and the residual negative pressure as a pressure drop proportional to the residual stress of the material, and (i) calculating the residual stress$_{(No\ Flow)}$ of the material based on the equation for determining the shear stress $_{(Flow)}$ for the geometry of the restricted passageway using the pressure drop in step (h).

It should be noted that instead of requiring a constant value as in steps (b) and (e), residual pressure or torque after an arbitrary (predetermined) time or rate of change, would also provide a measure of the yield stress.

These and other features and objects of the invention will become apparent from a consideration of the detailed description.

Figure 3:
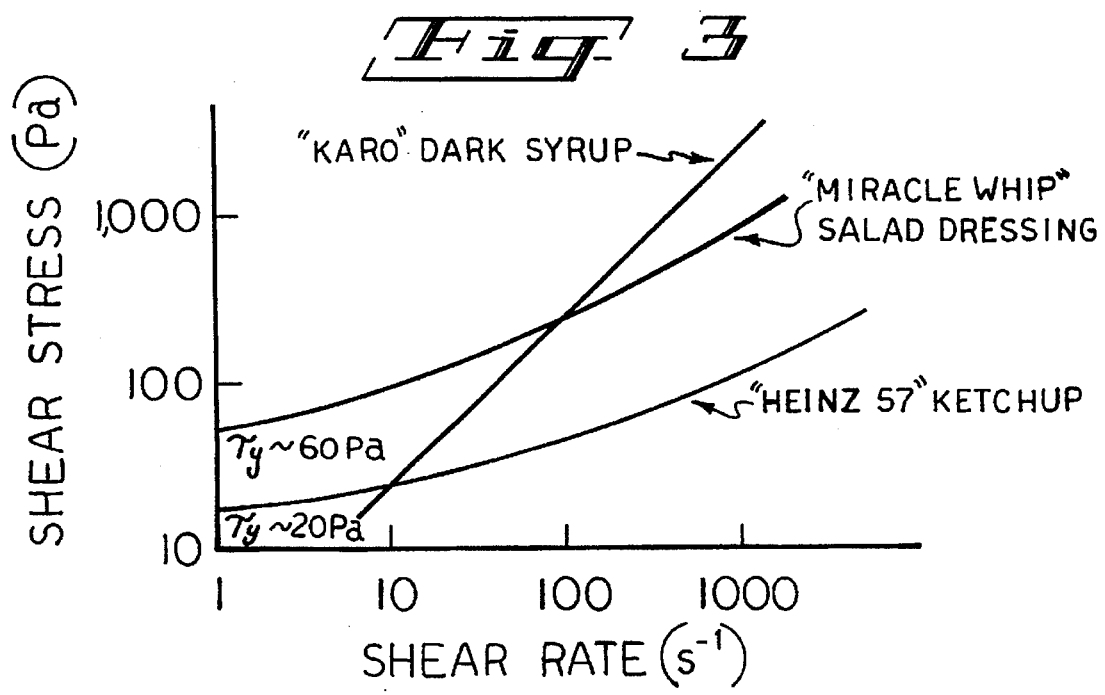
FIG. 3 is another graphical representation, similar to FIG. 2, but showing the flow behavior for some common food products. The Newtonian SYRUP (i.e. no yield stress) has a higher viscosity at high shear rate, while the SALAD DRESSING and the KETCHUP show a yield stress and a much higher viscosity at low shear rates. Plastic materials like the salad dressing and the ketchup show little or no deformation up to a certain level of stress. Above this yield stress, the material flows readily.

For example, to exceed the yield stress of the ketchup in the neck of a bottle, one must frequently tap the bottle. When the shear stress at the wall exceeds the yield stress, flow is rapid. For the ketchup in FIG. 3, the yield stress (tau$_y$) is 200 dynes/cm$^2$ (20 Pa). For the salad dressing in FIG. 3, the yield stress (tau$_y$) is 600 dynes/cm$^2$ (60 Pa).

DETAILED DESCRIPTION

The term "polymeric material" is used herein to include any viscous stream such as a fluid, gum, rubber, paste, sealant, elastomer, caulk, adhesive, resin, coating, or personal care formulation (i.e., a lotion, cream, emulsion, or microemulsion, for example). For illustrating the method in the example below, a silicone sealant mixture was selected as the polymeric material.

Silicone sealants typically contain a polydiorganosiloxane, a filler, a cross-linker, and a curing catalyst. These silicone sealants cure by exposure to moisture, and are viscous materials which can be extruded from cartridges into cracks or crevices to be sealed. The consistency of a silicone sealant is viscous and toothpaste-like. In applications such as building construction, silicone sealants are thixotropic and non-sagging in order to remain in place until cured. Because silicone sealants are used in building construction, aesthetics such as color are important. Therefore, silicone sealants of a variety of colors are used commercially.

Silicone sealants are made by mixing various ingredients in predetermined defined weight or volume ratios. For room temperature vulcanizable silicone sealants (RTV), polydiorganosiloxanes are end-blocked with silanol or other appropriate hydrolyzable groups. These polydiorganosiloxanes typically have a viscosity in excess of one Pa.s (1,000 centistoke) measured at 25° C., preferably 1 to 100 Pa.s (100,000 centistoke). When a filler is added to the polydiorganosiloxane, the mixture is called a "sealant base", since it constitutes the major portion of the silicone sealant, and because other ingredients are added to arrive at a final composition. Useful fillers are (i) reinforcing fillers such as silica and carbon black; and (ii) non-reinforcing or semi-reinforcing fillers such as titanium dioxide, quartz, diatomaceous earth, finely divided calcium carbonate, and alumina.

To the "sealant base", cross-linking agents and catalysts are added. The cross-linking agents are generally silanes or partial hydrolysis products of silanes. These silanes include acetoxysilanes, alkoxysilanes, ketoximosilanes, aminosilanes, and amidosilanes. The cross-linking silanes have three to four hydrolyzable groups per molecule, while the partial hydrolysis products have more than three. In addition to cross-linking agents, silicone sealants include chain-extending agents which are also silanes, but with only two hydrolyzable groups per molecule. The hydrolyzable group terminating the polydiorganosiloxane is often the same as the group of the silane cross-linking agent, but mixtures of different types of hydrolyzable groups can be present in the same silicone sealant mixture.

Catalysts for curing the silicone sealant mixtures are dependent upon the type of cross-linking agent, and include compounds such as metal carboxylates, alkyl orthotitanates, titanate chelates, and zirconium alkoxides and chelates.

Since the polydiorganosiloxane in the silicone sealant base is clear and colorless, coloring agents are often added. While silicone sealants can be clear, they are usually produced in five to eight standard colors, including black, white, and various tones of beige, brown, or gray. Virtually any color or hue is possible, subject to the reproducibility of the pigment, the exactness of metering, and the thoroughness of mixing. These coloring agents, commonly called pigments, include various categories of inorganic and organic pigments.

For example, the most important inorganic coloring agents employed in silicone sealants are derived from iron oxide pigments, such as the yellow, brown, red, and black, iron oxides. Other synthetic inorganic pigments include for example, cadmium orange, chromium oxide green, manganese violet, and molybdate orange. Typical of numerous varieties of organic synthetic coloring agents for silicone sealants are Acid Red 52, Benzidine Yellow HR, Methyl Violet, Phthalocyanine Green and Blue, Pigment Brown 28, and Victoria Blue B.

To facilitate processing, the coloring agent is added to the "sealant base" in the liquid state. These pigment dispersions, color concentrates, and liquid colorants, are achieved by dispersing a pigment in a liquid carrier.

In the past, processes for coloring silicone sealants have been complicated by the fact that frequent changeovers from color to color are required. Thus, the "sealant base" was compounded, catalyzed, and packaged in drums or bulk containers. The containers were moved to a separate color production process area for pigmentation. Many different color pigments are needed to make the variety of colors and shades required in the market place. Therefore, matching a particular color would often require sophisticated blending of a number of pigments.

Typically, production personnel load the "sealant base" into a large mixer, and meter the necessary coloring agent into the mixer to produce the colored silicone sealant. The ingredients are mixed for a period of time, and inspected for color match using standard colorimetry technology. The addition of the pigment has to be carefully controlled, because pigments can cause degradation of the physical properties of the silicone sealant, if the amount of pigment exceeds certain concentration levels. When the color of the silicone sealant is determined to be correct, the silicone sealant is then moved to a proportioning machine where the silicone sealant is dosed into cartridges, drums, or pails, in a one-part volumetric dosing system.

During dosing, production personnel measure various physical properties of the silicone sealant "off-line" to insure its quality, and verify that the silicone sealant meets product and manufacturing specifications. This requires that production personnel sample the silicone sealant, send the sample to the plant laboratory for testing, and wait for confirmation by the laboratory that the silicone sealant meets production specifications. Such "off-line" procedures are costly and time consuming, contributing to an already lengthy manufacturing process, and waste otherwise valuable manufacturing time.

This invention could eliminate "off-line" testing for yield stress by providing direct "on-line" measurement. For example, it could be used as a substitute for the American Society for Testing and Materials (ASTM) "Standard Test Method for Slump of Sealants", Designation D 2202-93a (Annual Book of ASTM Standards Volume 04.07), where samples of viscous material are placed on a flat horizontal surface having a graduated scale, the surface is raised to the vertical, and the distance of travel (or slump) of the viscous material down the vertical surface is measured. It could also be a suitable substitute for penetrometer yield tests used in measuring physical properties of materials.

Figure 1:
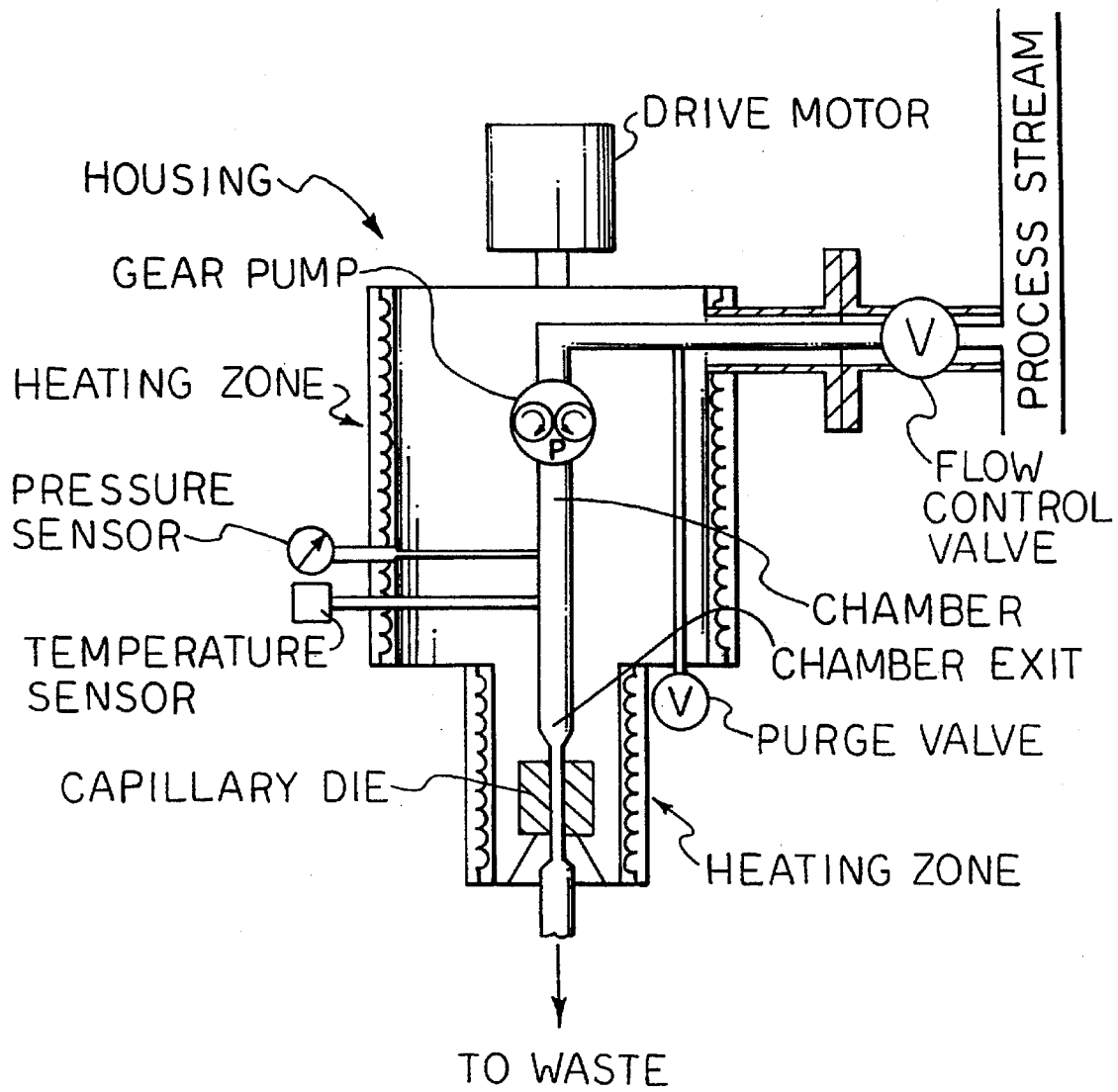
FIG. 1 is a pictorial representation of one type of commercially available capillary rheometer including various components of the system necessary to carry out the method of the invention.
Figure 2:
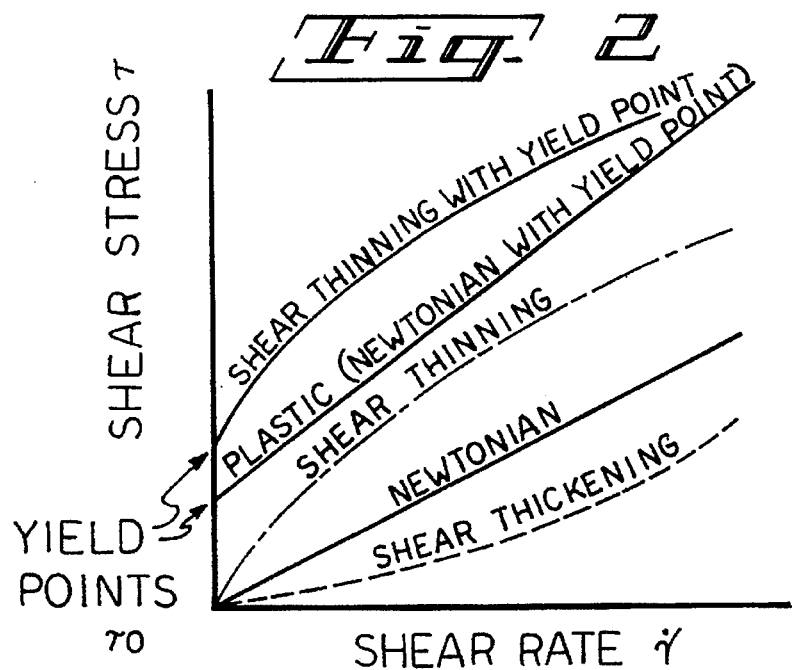
FIG. 2 is a graphical representation of shear stress plotted against shear rate for some common types of flow behavior referred to above in the BACKGROUND section. The yield stress (tau$_o$), where appropriate, is shown on the y axis (i.e., the shear stress coordinate). Viscosity is defined as the shear stress divided by the shear rate at any point.

Thus, with reference to FIG. 1 of drawing, there is depicted one form of capillary rheometer device suitable for practicing the method. The device will be seen to comprise a cylindrical HOUSING having a HEATING ZONE. The HEATING ZONE can be controlled to provide temperatures in the range of 60°–350° C. A positive displacement GEAR PUMP is arranged within the HEATING ZONE, and is driven by a DRIVE MOTOR (i.e., a servo-motor) mounted on the top of the HOUSING. The DRIVE MOTOR is capable of generating a speed of 0.1–100 RPM. The heated HOUSING contains a CHAMBER having a CHAMBER EXIT. The CHAMBER EXIT is in fluid communication with a CAPILLARY DIE located in the lower portion of the heated HOUSING. The CAPILLARY DIE is removably mounted within the HOUSING in the HEATING ZONE. Typically, the geometry of the CAPILLARY DIE provides for lengths/diameters of 20/1, 20/2, 20/3, 20/4, 40/1, 40/2, 40/3, and 40/4, millimeters, respectively; although dies are available with lengths/diameters of 60/1 to 20/4 millimeters. The device in FIG. 1 is especially designed for finishing and compounding processes in which there are frequent product changes. It allows easy access to the CAPILLARY DIE, which can be changed with a minimum of downtime.

The process stream, i.e., a silicone sealant mixture, is tapped from the pressurized main PROCESS STREAM, and is in fluid communication with the inlet of the GEAR PUMP by means of a FLOW CONTROL VALVE. A PURGE VALVE located downstream of the FLOW CONTROL VALVE is used to (i) vent air from the lines, (ii) withdraw samples of material from the lines, (iii) deliver material from the process line to the GEAR PUMP more rapidly for testing, or (iv) to purge the lines of materials previously pumped through the system. Temperature and pressure conditions existing within the CHAMBER between the outlet of the GEAR PUMP and the inlet of the CAPILLARY DIE are monitored by means of pressure and temperature sensors. A PRESSURE SENSOR such as a 50 bar transducer can be employed. The TEMPERATURE SENSOR can be a thermocouple for directly measuring the melt temperature in the melt channel. Materials passing through the CAPILLARY DIE can be sent TO WASTE as shown in FIG. 1, or the materials can be recirculated back to the PROCESS STREAM.

The following example illustrates the invention in more detail. The silicone sealant used as the PROCESS STREAM in this example was a mixture containing a polydiorganosiloxane end-blocked with silanol, a filler, and an acetoxysilane. Such silicone sealant mixtures are described in U.S. Pat. Nos. 3,035,016 (May 15, 1962), 3,077,465 (Feb. 12, 1963), 3,274,145 (Sep. 20, 1966), and 4,115,356 (Sep. 19, 1978), considered incorporated herein by reference.

Generally, sealant systems of this type can be represented by the reaction sequence:

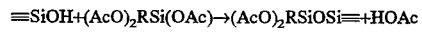

$$\equiv SiOH + (AcO)_2RSi(OAc) \rightarrow (AcO)_2RSiOSi\equiv + HOAc$$

where Ac is $CH_3CO-$. These mixtures can vary from viscous fluids to thick viscous pastes, and are curable to rubbery materials or elastomers when exposed to moisture.

EXAMPLE I

What led to this experiment was the problem of establishing repeatable, precise zeroing, of a capillary rheometer. It was surmised that the problem may have been due to a residual pressure and stress related to the yield stress of the silicone sealant mixture contained in the capillary rheometer. In prior experiments, it had been noted that when the capillary die was removed from the rheometer, or when the capillary die was re-inserted into the rheometer, the procedure had an impact on the zero value. The impact was in the direction and of an approximate magnitude expected for the yield stress of the silicone sealant mixture corresponding to a capillary die with a diameter of one millimeter and a length of forty millimeters.

It was decided that, to confirm yield stress effect, the pump should be shut off with the capillary die in the rheometer, and the "zero" noted. Then it was decided to manually reverse the pump a small amount, and to note a new "zero". The difference between these two "zero" values would therefore correspond to twice the yield stress; and their average would be a true "zero" point for the system.

This procedure of obtaining readings in opposite flow directions takes into account and eliminates the drift factor often found in pressure sensors and pressure gauges. Thus, under ideal conditions, gauges in empty pipes with no flow read 0.00. Under non-ideal conditions, however, gauges often drift with time from a true zero value to either a positive or negative value. Therefore a true reading can be obtained regardless of drift by measuring the value which is one-half of the difference between two readings taken in opposite directions.

Accordingly, it was found that this residual pressure within a GOETTFERT Model MBR Capillary Rheometer, depicted schematically in FIG. 1, after gear pump stoppage, resulted from the yield stress of the silicone sealant mixture. By measuring this residual stress, a calculation of yield stress based on capillary die geometry (i.e., its configuration) was made. The capillary die used in the experiment had a length of forty millimeters and a diameter of one millimeter. Measurements were made at a temperature of 50° C.

The data recorded during the experiment is shown in Table I. By way of explanation, in the Table, values 17.2 bar at time 9:05 and 17.1 bar at time 9:37, are measurements of flow stress or shear stress of the material. Residual stress on the other hand, is measured under conditions of no flow, and is reflected by pressure sensor readings at times indicated as "No flow".

TABLE I

| Time | Condition of Pump | Pressure Sensor Reading (bar) |
|---|---|---|
| 8:43–8:48 | Flow in forward direction at 2.0 cc/minute | — |
| 8:53 | No flow for 5 minutes | +0.15 |
| 8:54 | Reversed ¼ turn (about 0.05 cc) | — |
| 9:02 | No flow for 8 minutes | −0.34 |
| 9:05–9:20 | Running forward at 2.0 cc/min | +17.20 |
| 9:21 | No flow for one minute | +0.20 |
| 9:24–9:30 | Reversed one turn (about 0.2 cc) | — |
| 9:34 | No flow for 4 minutes | −1.07 |
| 9:35–9:39 | Running forward at 2.0 cc/min | +17.10 |
| 9:41 | No flow for 3 minutes | +0.20 |

The residual stress, expected to relate to the yield stress of the acetoxy silicone sealant mixture used in this example, can be calculated by (i) determining half the difference between the positive backpressure and the negative backpressure as the pressure drop (P) through the capillary passageway, and (ii) calculating the residual stress of the polymeric material according to the relationship $$\text{Residual Stress}_{(No\ Flow)} = RP/2L$$

where R is the radius of the capillary passageway, L is the length of the capillary passageway, and P is the pressure drop through the capillary passageway.

Thus, as a first example in Table I, $$\text{Residual Stress}_{(No\ Flow)} = \frac{(0.5\ mm)\frac{[+0.15 - (-0.34)]}{2}}{2(40\ mm)} = 0.0015\ bar$$

As a second example in Table I, $$\text{Residual Stress}_{(No\ Flow)} = \frac{(0.5\ mm)\frac{[+0.20 - (-1.07)]}{2}}{2(40\ mm)} = 0.0040\ bar$$

Given the fact that the pressure sensor used in this experiment was a 50 bar ($50 \times 10^5$ Pascal) transducer, these much smaller residual pressures and the resulting variations in residual stress are considered acceptable within the limits and the capability of the equipment employed. An average of these values provides a good estimate of yield stress, even though additional readings were not obtained.

The advantages of obtaining forward and reverse (dual) readings are that (i) the rheometer system becomes insensitive to calibration errors, and (ii) the forward and reverse measurement has a larger range than methods using forward (single) measurements. While single and dual methods each result in measurement of residual (yield) stress, the forward and reverse (dual) measurement provides greater precision and accuracy.

While the method has been demonstrated herein using a capillary die, the rheometer can be modified to force polymeric material through a thin rectangular channel or slit, a square die, or a tapered die. For example, except for numerical constants, equations for calculating the shear rate for slit rheometry are the same as for capillary rheometry. The working equation for a slit rheometer pertinent to the invention is shown below:

$$\text{Residual Stress}_{(No\ Flow)} = \frac{HP}{2(1 + H/W)L}$$

where H is the thickness of the slit, P is the pressure drop across the slit, W is the width of the slit, and L is the length of the slit.

In addition, the method can be used in torque recording rheometers such as Couette-type rheometers, cone and plate rheometers, and parallel plate rheometers, for example.

Other variations may be made in the compounds, compositions, methods, and apparatus, described herein without departing from its essential features. The forms of invention are exemplary only and not intended as limitations on the scope defined in the claims.

We claim:

1. A method of measuring a pressure drop which is proportional to the yield stress of a material, the method comprising:
    (a) flowing the material in a forward direction through a chamber having an exit through a restricted passageway so as to produce a positive pressure in the chamber,
    (b) stopping the forward flow of material into the chamber and allowing the residual positive pressure in the chamber to stabilize and reach a constant value,
    (c) recording the residual positive pressure in the chamber under no flow conditions at the constant value reached in step (b),
    (d) withdrawing material from the chamber so as to produce a negative pressure and initiate a reverse flow of material into the chamber through the restricted passageway,
    (e) stopping the withdrawal of material from the chamber and allowing the negative pressure to stabilize and reach a constant value,
    (f) recording the residual negative pressure in the chamber under no flow conditions at the constant value reached in step (e), and
    (h) determining half the difference between the residual positive pressure and the residual negative pressure as a pressure drop proportional to the yield stress of the material.

2. A method according to claim 1 wherein the pressure drop is determined on-line while the material is part of a process stream.

3. A method according to claim 2 wherein the material is a silicone sealant mixture.

4. A method according to claim 2 wherein the restricted passageway is a capillary passageway, a rectangular channel, a slit channel, a square channel, or a tapered passageway.

5. A method of measuring a pressure drop which is proportional to the yield stress of a material, the method comprising:
    (a) flowing the material in a forward direction through a chamber having an exit through a restricted passageway so as to produce a positive pressure in the chamber,
    (b) stopping the forward flow of material into the chamber and allowing the residual positive pressure in the chamber to stabilize and reach a constant value, (c) recording the residual positive pressure in the chamber under no flow conditions at the constant value reached in step (b), (d) withdrawing material from the chamber so as to produce a negative pressure and initiate a reverse flow of material into the chamber through the restricted passageway, (e) stopping the withdrawal of material from the chamber and allowing the negative pressure to stabilize and reach a constant value, (f) recording the residual negative pressure in the chamber under no flow conditions at the constant value reached in step (e), (h) determining half the difference between the residual positive pressure and the residual negative pressure as a pressure drop proportional to the yield stress of the material, and (i) calculating the residual stress$_{(No\ Flow)}$ of the material based on the equation for determining the shear stress $_{(Flow)}$ for the geometry of the restricted passageway using the pressure drop in step (h).

6. A method according to claim 5 wherein the pressure drop is determined on-line while the material is part of a process stream.

7. A method according to claim 6 wherein the material is a silicone sealant mixture.

8. A method according to claim 6 wherein the restricted passageway is a capillary passageway, a rectangular channel, a slit channel, a square channel, or a tapered passageway.

9. A method according to claim 8 wherein the restricted passageway is a capillary, and the residual stress of the material is calculated according to the relationship $$\text{Residual Stress}_{(No\ Flow)} = RP/2L$$

where R is the radius of the capillary passageway, L is the length of the capillary passageway, and P is the pressure drop in step (h).

10. A method according to claim 8 wherein the restricted passageway is a rectangular channel or a slit channel, and the residual stress of the material is calculated according to the relationship $$\text{Residual Stress}_{(No\ Flow)} = \frac{HP}{2(1 + H/W)L}$$

where H is the thickness of the rectangular channel or slit channel, P is the pressure drop in step (h), W is the width of the rectangular channel or slit channel, and L is the length of the rectangular channel or slit channel.

* * * * *